(12) United States Patent
Eisner et al.

(10) Patent No.: US 10,398,541 B2
(45) Date of Patent: Sep. 3, 2019

(54) SYSTEM AND METHOD FOR USE OF FLEXIBLE ANTI-REFLUX URETERAL STENT

(71) Applicants: Brian H. Eisner, Boston, MA (US); Scott Miller, Arlington, VA (US)

(72) Inventors: Brian H. Eisner, Boston, MA (US); Scott Miller, Arlington, VA (US)

(73) Assignee: The General Hospital Corporation, Boston, MA (US)

( * ) Notice: Subject to any disclaimer, the term of this patent is extended or adjusted under 35 U.S.C. 154(b) by 17 days.

(21) Appl. No.: 14/774,513

(22) PCT Filed: Mar. 13, 2014

(86) PCT No.: PCT/US2014/025321
§ 371 (c)(1),
(2) Date: Sep. 10, 2015

(87) PCT Pub. No.: WO2014/159848
PCT Pub. Date: Oct. 2, 2014

(65) Prior Publication Data
US 2016/0038273 A1 Feb. 11, 2016

Related U.S. Application Data

(60) Provisional application No. 61/782,272, filed on Mar. 14, 2013.

(51) Int. Cl.
*A61F 2/04* (2013.01)
*A61M 27/00* (2006.01)

(52) U.S. Cl.
CPC .............. *A61F 2/042* (2013.01); *A61F 2/04* (2013.01); *A61M 27/008* (2013.01);
(Continued)

(58) Field of Classification Search
CPC ...... A61F 2002/048; A61F 2/04; A61F 2/042; A61F 2250/0014; A61F 2250/0019; A61F 2/24
See application file for complete search history.

(56) References Cited

U.S. PATENT DOCUMENTS 3,830,240 A 8/1974 Antonevich et al.
4,874,360 A 10/1989 Goldberg et al.
(Continued)

FOREIGN PATENT DOCUMENTS

CN 203988361 U 12/2014
WO 2010068467 A1 6/2010

OTHER PUBLICATIONS

International Search Report and Written Opinion dated Jul. 18, 2014 in connection with PCT/US2014/025321.
(Continued)

*Primary Examiner* — Brian E Pellegrino
(74) *Attorney, Agent, or Firm* — Quarles & Brady LLP

(57) ABSTRACT

The multi-material stent includes a renal portion and a bladder portion with respective, different hardness. A valve is disposed within the stent to guide liquid from the renal portion of the stent to the bladder portion of the stent. The present invention relates towards systems and method for stents. More particularly, the invention relates to a stent designed to increase patient comfort by minimizing irritation and reflux through the use of a stent that incorporates one or more flexible elements, which may involve materials with varying degrees of hardness, and a valve disposed therein.

17 Claims, 7 Drawing Sheets

(52) U.S. Cl.
CPC ... *A61F 2002/047* (2013.01); *A61F 2002/048* (2013.01); *A61F 2230/0069* (2013.01)

(56) References Cited

U.S. PATENT DOCUMENTS

| | | | |
|---|---|---|---|
| 5,476,450 A | 12/1995 | Ruggio | |
| 5,827,229 A | 10/1998 | Auth et al. | |
| 6,395,021 B1 * | 5/2002 | Hart | A61F 2/042 604/8 |
| 7,540,868 B2 | 6/2009 | Elliott et al. | |
| 7,883,515 B2 | 2/2011 | Kear | |
| 8,192,500 B2 | 6/2012 | Chung | |
| 8,672,928 B2 | 3/2014 | Liu et al. | |
| 9,789,293 B2 * | 10/2017 | Teague | A61M 27/008 623/23.7 |
| 2003/0199986 A1 * | 10/2003 | McWeeney | A61F 2/0022 623/23.7 |
| 2003/0216760 A1 | 11/2003 | Welch et al. | |
| 2004/0019358 A1 | 1/2004 | Kear | |
| 2004/0153095 A1 | 8/2004 | Seddon | |
| 2004/0267213 A1 | 12/2004 | Knapp | |
| 2005/0149201 A1 | 7/2005 | Mcweeney et al. | |
| 2007/0296069 A1 | 12/2007 | Buca-Couto et al. | |
| 2007/0298069 A1 | 12/2007 | Bucay-Couto et al. | |
| 2008/0004578 A1 * | 1/2008 | Hixon | A61L 31/148 604/326 |
| 2010/0137846 A1 | 6/2010 | Desai et al. | |
| 2010/0160848 A1 * | 6/2010 | Ostrovsky | A61F 2/042 604/8 |
| 2010/0305475 A1 | 12/2010 | Hinchliffe et al. | |
| 2011/0060315 A1 | 3/2011 | Windheuser et al. | |
| 2011/0224489 A1 | 9/2011 | Deal | |
| 2011/0245841 A1 | 10/2011 | Shohat et al. | |
| 2012/0184893 A1 * | 7/2012 | Thompson | A61F 2/04 604/9 |
| 2013/0024003 A1 | 1/2013 | McWeeney et al. | |
| 2016/0001050 A1 * | 1/2016 | Yee | A61M 27/008 604/8 |

OTHER PUBLICATIONS

Villanueva, et al., Silicone Catheters May Be Superior to Latex Catheters in Difficult Urethral Catheterization After Urethral Dilation, Journal of Endourology, 2011, 25(5):841-844.
PCT International Search Report and Written Opinion, PCT/US2014/026037, dated Sep. 16, 2014.
European Patent Office, Extended European Search Report, Application No. 14775184.6, dated Nov. 17, 2016.

* cited by examiner

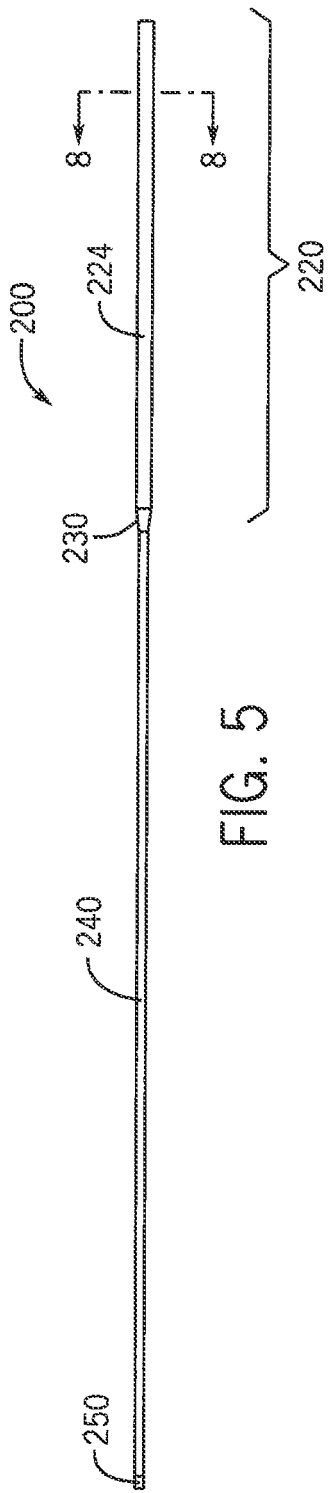
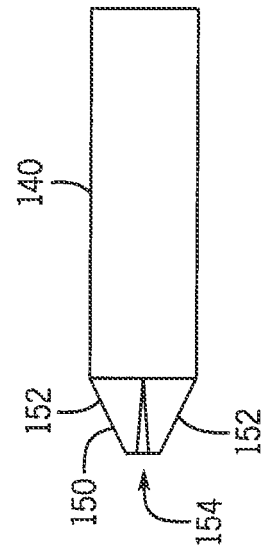
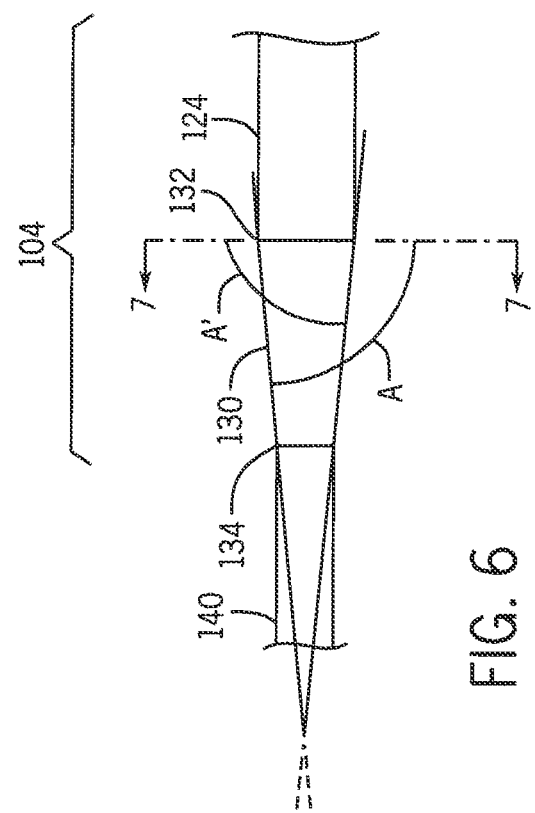
FIG. 5
FIG. 7
FIG. 6

SYSTEM AND METHOD FOR USE OF FLEXIBLE ANTI-REFLUX URETERAL STENT

CROSS-REFERENCE TO RELATED APPLICATIONS

The present application represents the national stage entry of PCT International Application No. PCT/US2014/025321 filed Mar. 13, 2014, which is based on, and claims priority to U.S. Provisional Application Ser. No. 61/782,272, filed Mar. 14, 2013, both of which are incorporated herein by reference in their entirety for all purposes.

STATEMENT REGARDING FEDERALLY SPONSORED RESEARCH

N/A

BACKGROUND OF THE INVENTION

The present invention relates towards systems and method for stents. More particularly, the invention relates to a stent designed to increase patient comfort by minimizing irritation and reflux through the use of a stent that incorporates one or more flexible elements, which may involve materials with varying degrees of hardness, and a valve disposed therein.

Stents are thin, hollow tubes inserted into a conduit in a patient to assist in opening a passageway that has been obstructed, or to assist in maintaining a passageway between two localized areas in the patient. Stents may be used to prevent flow constriction and to allow access for surgical procedures. One specific type of stent, a ureteral stent, is used to maintain a passageway between a patient's kidneys and bladder due to complications from infection, tumors, kidney stones, or other conditions that impact the urinary tract. In particular, a ureteral stent is inserted into the ureter to assist in draining urine from the patient's kidney to the patient's bladder if there is a blockage or other condition that does not allow for normal urine flow. Stents are also routinely inserted into a patient's ureter for several days after ureteroscopic kidney stone surgery to remove kidney or ureteral stones. Stents are designed to be positioned within a patient for days or weeks until the blockage is removed or normal urine flow is otherwise restored.

There are numerous problems and side effects associated with existing ureteral stents, however. One such problem is migration of the stent after insertion such that the stent does not remain in the specified location over the duration that the stent is disposed within the patient. To combat migration issues in stents, typical ureteral stent designs (e.g., double J) utilize coils at opposing proximal and distal ends of the stent to anchor the stent in the patient's kidney and bladder, respectively. Stents utilizing a double J design are more successful in retaining the ureteral stent in the desired location in the patient, but cause various other undesirable side effects due to the lower coil being disposed adjacent to and aggravating the patient's bladder. For example, the lower coil frequently causes the patient to suffer from bleeding, urges to pass urine frequently, and burning while passing urine due to the coil scratching the bladder.

An additional consideration for a ureteral stent is the desirability to control urine reflux that occurs during urination while using a stent. Stents frequently include at least one hollow tube (e.g., a lumen) so typically some amount of urine refluxes back into the patient's kidneys during and after urination as opposed to exiting from the body. Existing ureteral stents have insufficient mechanisms to control reflux that also allow for urine flow to pass from the patient. Reflux may cause pain (sometimes severe) in some patients and may lead to serious health conditions including urinary tract infections and even renal failure in extreme cases.

Attempts have been made to modify ureteral stent design to overcome the aforementioned problems to prohibit migration of the stent while minimizing patient discomfort. For example, one such stent incorporates a coiled end portion designed to reside in the patient's kidney and terminates at one or more flexible loops. The stent is substantially rigid throughout the length thereof until terminating at the loops. However, significant drawbacks exist with this stent design. For example, the stent includes a significant portion of rigid material that irritates the patient's urinary tract and results in patient discomfort. Further, this stent design does not include a mechanism to control reflux.

SUMMARY OF THE INVENTION

The present invention overcomes the aforementioned drawbacks by providing a stent including one or more flexible elements which may be achieved by materials having different hardness properties or by a single material with different types of reinforcement and/or thicknesses, and whereby the stent incorporates a self-retaining securement mechanism to assist in preventing migration. The self-retaining securement mechanism is substantially more rigid than a majority of the rest of the stent and the softer material enhances patient comfort and minimizes patient irritation. The stent may further incorporate a valve therein to address reflux problems.

In one non-limiting configuration, a stent comprises a renal portion having a hardness characterized between about 20 Shore A to about 90 Shore A. A bladder portion has a hardness characterized between about 5 Shore A to about 60 Shore A. A valve is disposed within the stent to guide liquid from the renal portion of the stent to the bladder portion of the stent.

In a different configuration, a stent includes an elongate conduit defined by a renal portion and a bladder portion. A valve is disposed within the conduit, and between about 75% to about 99% of the conduit is characterized by a hardness of less than about 80 Shore A. The valve facilitates fluid flow only in one direction through the conduit.

In a further configuration, a stent includes a self-retaining securement mechanism having a first hardness value. A flexible tube defining a bladder portion has a second hardness value, wherein the first hardness value is greater than that of the second hardness value. A valve is disposed in the stent.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5 is a side elevational view of a different embodiment of a stent;

FIG. 6 is a portion of a connector portion of the stent of FIG. 5 enlarged for magnification purposes;

FIG. 7 is a portion of a tip of the stent of FIG. 5 enlarged for magnification purposes;

DETAILED DESCRIPTION OF THE INVENTION

Figure 1:
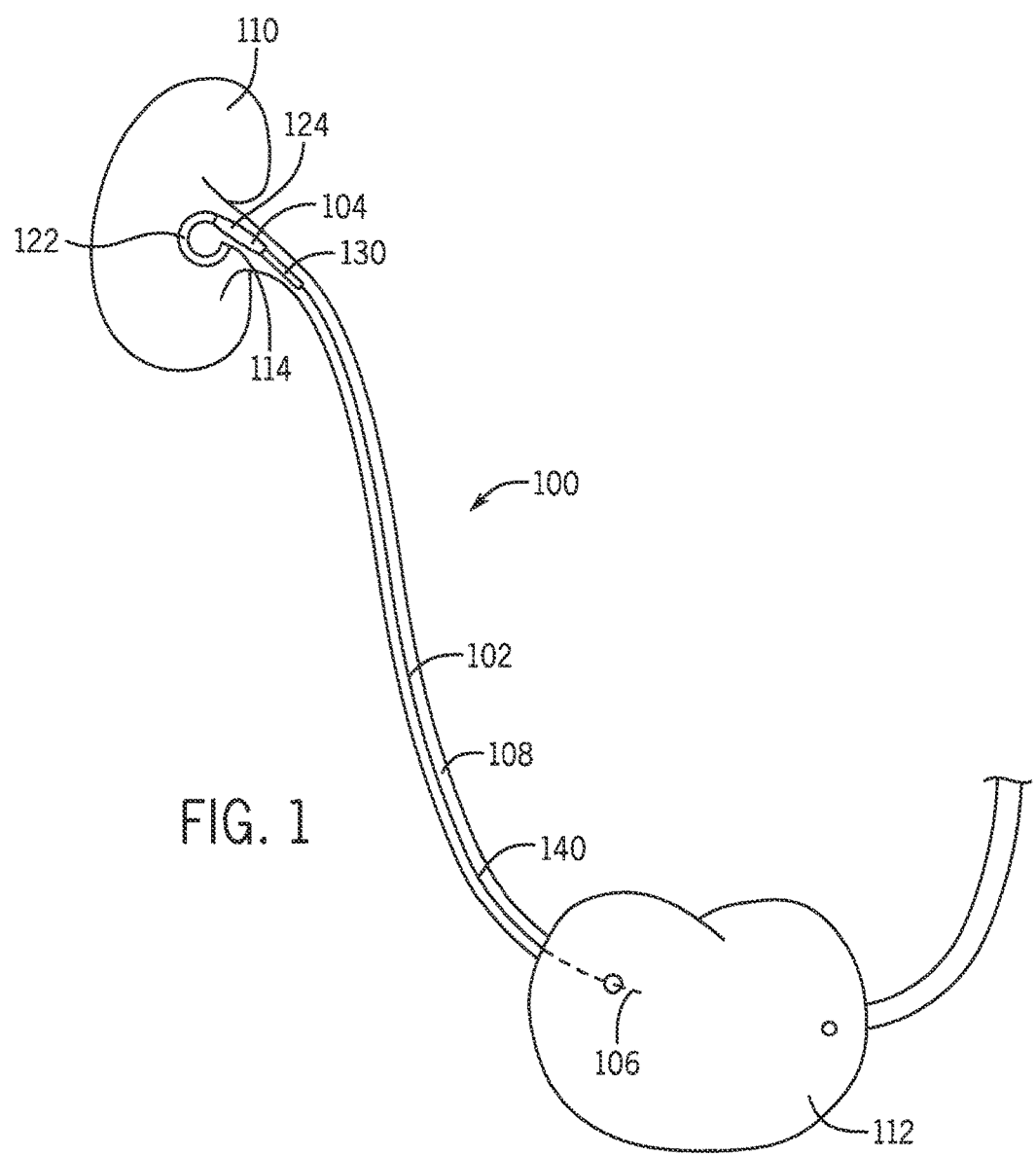
FIG. 1 is a partial schematic view depicting a possible installation of a ureteral stent in a urinary tract of a patient.

As best seen generally in FIGS. 1-14, a stent 100 includes an elongate conduit 102 having a renal portion 104 and a bladder portion 106. The elongate conduit 102 defines at least one lumen, which allows fluid communication therethrough. The stent 100 is designed to be placed or otherwise positioned in a passageway of a patient (e.g., urinary tract), and in particular, into a patient's ureter 108. The renal portion 104 of the stent 100 is designed to be positioned proximate the patient's kidney 110 and the bladder portion 106 is designed to be positioned proximate the patient's bladder 112. The stent 100 provides a passageway from the kidney 110 to the bladder 112 through the ureter 108 to allow urine to flow unimpeded and exit from the patient through the urethra (not shown).

In one embodiment, the stent 100 is defined by at least two separate materials having a different hardness parameter as discussed herein. In a different embodiment, the stent 100 is defined by the same material over the length thereof that have varying diameters to provide different hardness characteristics along the length thereof. For example, in one embodiment, the renal portion 104 and the bladder portion 106 include different materials, wherein the bladder portion 106 is defined by a hardness characteristic less than that of the renal portion 104. In a different embodiment, the renal portion 104 and the bladder portion 106 are characterized by the same material. In this embodiment, portions (or all) of the bladder portion 106 are defined by a diameter parameter smaller than that of the renal portion 104 such that the bladder portion 106 is more flexible due to the smaller size. In still a further embodiment, the renal portion 104 and the bladder portion 106 each include a different material and are characterized by a different diameter parameter with respect to each other.

The total length of the stent 100 may be selected with respect to numerous factors including the size of the patient. In one embodiment, the stent 100 is defined by a length dimension of between about 15 cm to about 40 cm as measured from a first end 114 of the renal portion 104 to a second end 116 at the bladder portion 106. The length dimension may be more preferably between about 18 cm to about 35 cm, and most preferably between about 22 cm to about 28 cm. Although it should be appreciated that the length of the stent 100 may be adjusted as desired.

Figure 3:
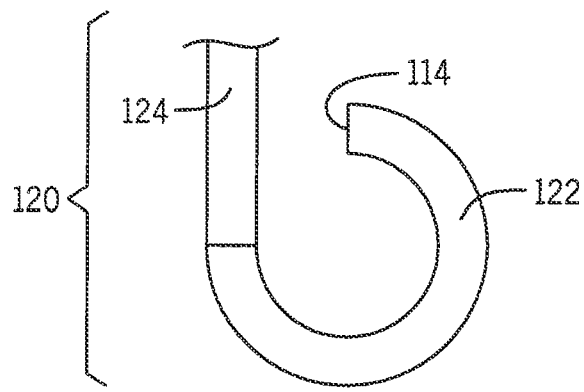
FIG. 3 is a portion of a self-retaining securement mechanism of the stent of FIG. 2 enlarged for magnification purposes.
Figure 4:
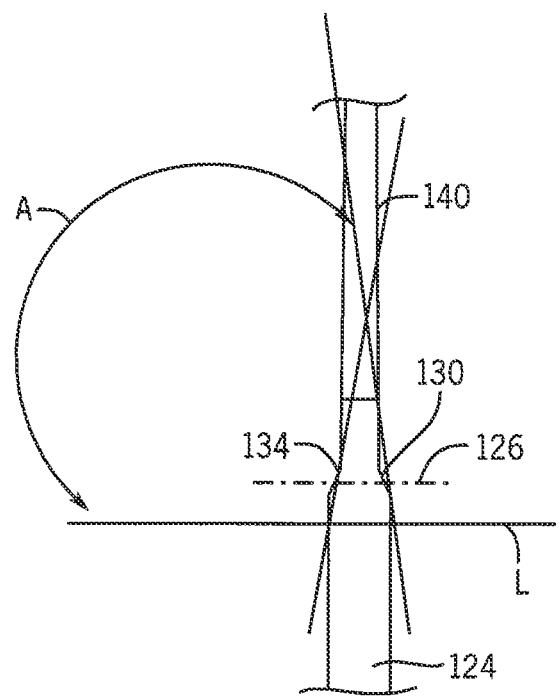
FIG. 4 is a portion of the self-retaining securement mechanism of FIG. 3 and a connector portion of the stent of FIG. 2 enlarged for magnification purposes.
Figure 8:
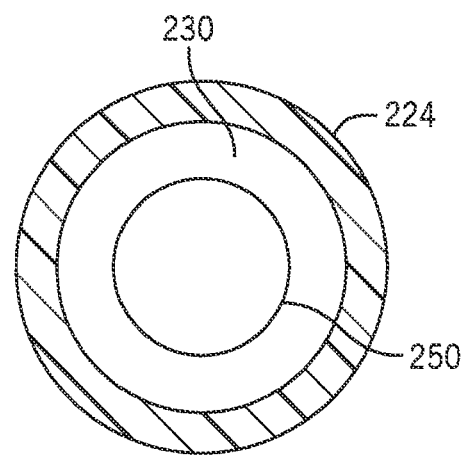
FIG. 8 is a cross-sectional view of an end of the stent of FIG. 5 adjacent a self-retaining securement mechanism taken generally along the lines 8-8 of FIG. 5.
Figure 9:
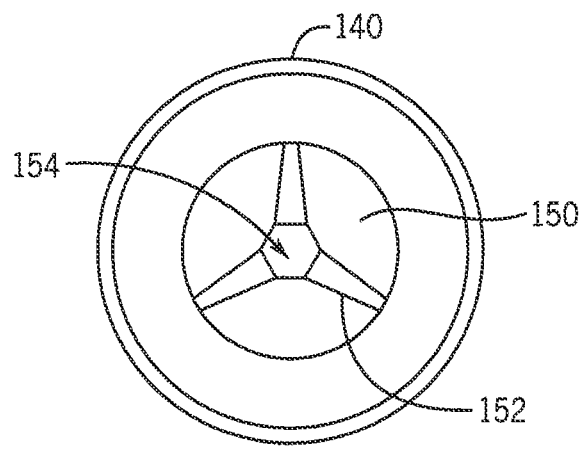
FIG. 9 is a front axial view of the stent of FIG. 5.

As best seen in FIG. 3, the stent 100 includes a self-retaining securement mechanism 120 disposed on the renal portion 104 thereof. The self-retaining securement mechanism 120 includes a rounded J-shaped coil 122 that terminates at a straightened portion 124. The self-retaining securement mechanism 120 is designed to be located adjacent the kidney 110 and to securely anchor the stent 100 thereto. In one embodiment, the self-retaining securement mechanism 120 is defined by the single J-shaped coil 122 extending therefrom (see FIG. 3). In a different embodiment, the self-retaining securement mechanism 120 includes other types of pigtail or spiral coils (not shown) as known in the art. In another embodiment, the self-retaining securement mechanism 120 may be substantially straight (see FIGS. 5 and 10). In a further embodiment, the self-retaining securement mechanism 120 includes other structures and/or shapes that assist in retaining the stent 100 in the kidney 110.

In one embodiment, the self-retaining securement mechanism 120 includes a rigid material as compared to the other portions of the stent 100 or the same material, but applied in way that results in greater rigidity, such as through layering the material or adding additional support to the material, such as through a wire or other reinforcement addition. For example, suitable materials for use as the self-retaining securement mechanism 120 include any biocompatible materials having the hardness defined herein. Examples of suitable materials for the self-retaining securement mechanism 120 include polymers and copolymers such as polyurethane, polyamides, and various ethylene copolymers and block copolymers (e.g., ethyl vinyl acetate (EVA)). Other useful materials include biocompatible plastics, e.g., polyester, nylon based biocompatible polymers, polytetrafluoroethylene polymers, silicone polymers, polyurethane polymers, polyethylene polymers, and thermoplastic polymers.

The self-retaining securement mechanism 120 is preferably defined by hardness parameter of about 30 Shore A to about 80 Shore A as determined by the ASTM D-2240 method. In other embodiments, the self-retaining securement mechanism 120 includes a hardness parameter between about 20 Shore A to about 90 Shore A. In still other embodiments, the self-retaining securement mechanism 120 includes a material having other rigidity properties.

The self-retaining securement mechanism 120 is also defined by an outer diameter of between about 2 Fr. to about 12 Fr. and more preferably between about 4 Fr. to about 8 Fr. In one embodiment, the outer diameter of the self-retaining securement mechanism 120 is about 5 Fr. In a different embodiment, the outer diameter of the self-retaining securement mechanism 120 is about 6 Fr. In still a different embodiment, the outer diameter of the self-retaining securement mechanism 120 is about 7 Fr. Further, the self-retaining securement mechanism 120 includes an interior diameter of between about 0.01 Fr. to about 3 Fr. and more preferably between about 1 Fr. to about 2 Fr. In one embodiment, the interior diameter of the self-retaining securement mechanism 120 is about 2 Fr. In a different embodiment, the interior diameter of the self-retaining securement mechanism 120 is about 3 Fr. In still a different embodiment, the interior diameter of the self-retaining securement mechanism 120 is about 4 Fr. It should be recognized that a self-retaining securement mechanism 120 including a larger diameter may assist in preventing migration of the stent 100 from the kidney 110, however the increased thickness may also increase patient discomfort.

The self-retaining securement mechanism 120, which includes the J-shaped coil 122 and the straightened portion 124, preferably includes a length dimension from about 5 cm to about 20 cm as measured from the first end 114 of the J-shaped coil 122 to an end 126 of the straightened portion 124 (as measured when the coil is unwound and straightened). The length dimension of the self-retaining securement mechanism 120 is more preferably between about 8 cm to about 18 cm, and most preferably between about 12 cm to about 14 cm. Although it should be appreciated that the length of the self-retaining securement mechanism 120 may be adjusted as desired.

As best seen in FIG. 6, the straightened portion 124 of the self-retaining securement mechanism 120 is integral with a tapered connector conduit 130, and together collectively form the renal portion 104 of the stent 100. The tapered connector conduit 130 is defined by a truncated cone having a diameter at a proximal end 132 that is substantially similar to the outer diameter of the self-retaining securement mechanism 120. The connector conduit 130 tapers inwardly until terminating at a distal end 134 that includes an outer diameter that is substantially similar to an outer diameter of the bladder portion 106, discussed in more detail hereinbelow.

The connector conduit 130 includes a length dimension of between about 0.01 cm to about 6 cm, and more preferably between about 1 cm to about 2 cm. In one embodiment, the length dimension is about 0.5 cm. In a different embodiment, the length dimension is about 1 cm. In still a different embodiment, the length dimension is about 2 cm.

The connector conduit 130 includes an outer diameter of between about 2 Fr. to about 12 Fr., and more preferably between about 4 Fr. to about 8 Fr. at the proximal end 132 thereof. In one embodiment, the outer diameter of the connector conduit 130 is about 5 Fr. adjacent the proximal end 132. In a different embodiment, the outer diameter of the connector conduit 130 is about 6 Fr. at the proximal end 132. In still a different embodiment, the outer diameter of the connector conduit 130 is about 7 Fr. at the proximal end 132.

The connector conduit 130 tapers inwardly until having an outer diameter of between about 2 Fr. to about 6 Fr., and more preferably between about 3 Fr. to about 5 Fr. at the distal end 134 thereof. In one embodiment, the outer diameter of the connector conduit 130 is about 5 Fr. adjacent the distal end 134. In a different embodiment, the outer diameter of the connector conduit 130 is about 4 Fr. at the distal end 134. In still a different embodiment, the outer diameter of the connector conduit 130 is about 3 Fr. at the distal end 134.

The ratio of the diameter of the connector conduit 130 with respect to the outer diameter dimension measured at the proximal end 132 as compared to the distal end 134 is about 2 to about 1. In a different embodiment, the ratio of the connector conduit 130 with respect to the outer diameter dimension measured at the proximal end 132 as compared to the distal end 134 is about 3 to about 1. In still a different embodiment, the ratio of the connector conduit 130 with respect to the outer diameter dimension measured at the proximal end 132 as compared to the distal end 134 is about 3 to about 2. In a different embodiment, the ratio of the connector conduit 130 with respect to the outer diameter dimension measured at the proximal end 132 as compared to the distal end 134 is about 4 to about 3. Although it is contemplated that the connector conduit 130 may include a substantially uniform diameter over the length thereof, the narrowing of the connector conduit 130 assists in preventing urine reflux.

As best seen in FIG. 6, the connector conduit 130 tapers inwardly in substantially the same manner throughout the circumference thereof. In particular, angles A and A' are formed by an exterior surface of the connector conduit 130 as defined by a longitudinal axis L and an axis formed by the slope of the surface of the connector conduit 130. In one embodiment, the angles A and A' are between about 90 degrees to about 45 degrees, in a different embodiment, the angles A and A' are between about 60 degrees to about 88 degrees. In a further embodiment, the angles A and A' are between about 75 degrees to about 85 degrees. In one specific embodiment, the angles A and A' are about 85 degrees.

In one embodiment, the connector conduit 130 includes the same material as other portions of the self-retaining securement mechanism 120 (i.e., the coil 122 and/or the straightened portion 124). In a different embodiment, the connector conduit 130 includes a material similar to the material of the bladder portion 106 of the stent 100. In still a different embodiment, the connector conduit 130 includes a plurality of materials such that the hardness of the material of the connector conduit 130 lessens moving from the proximal end 132 to the distal end 134.

Figure 2:
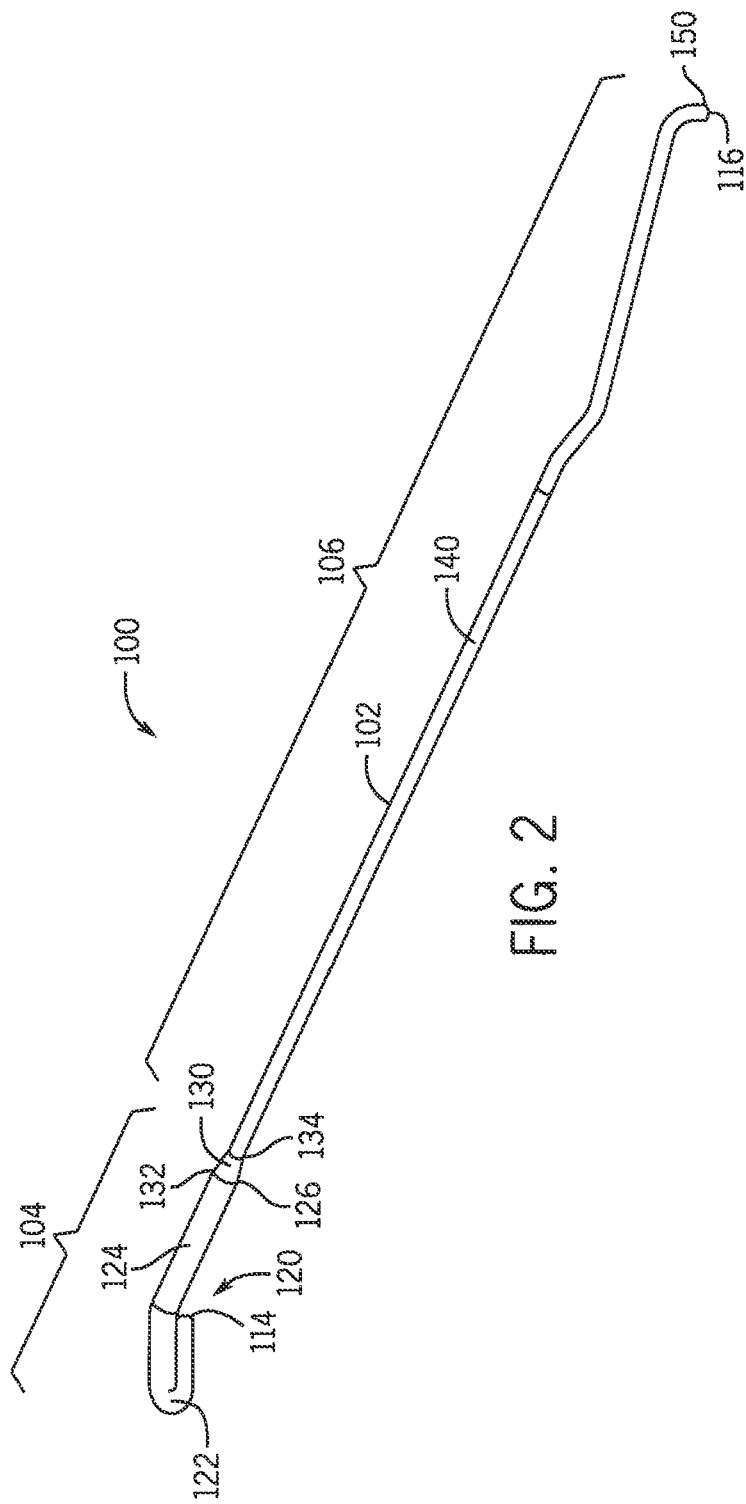
FIG. 2 is an isometric view of one type of a stent.

As best seen in FIG. 2, the distal end 134 of the connector conduit 130 is integral with and terminates at the bladder portion 106 of the stent 100. The bladder portion 106 includes a flexible tube 140 that defines a lumen including a relatively soft material as compared to the other portions of the stent 100. In particular, in one embodiment, the flexible tube 140 is defined by hardness of about 5 Shore A to about 60 Shore A. In other embodiments, the flexible tube 140 includes a hardness between about 10 Shore A to about 30 Shore A. In another embodiment, the tube 140 includes the same material as one or more other portions of the stent 100 (e.g., the renal portion 104). In still other embodiments, the flexible tube 140 may include a material having other rigidity properties.

Suitable materials for use as the flexible tube 140 include any biocompatible materials having the hardness defined herein. For example, in some embodiments, the flexible tube 140 of the stent 100 is constructed of a thermoplastic elastomer, or a natural or synthetic polymer such as silicone. It should be recognized that other materials may be utilized as desired, but that the hardness of the material(s) used for the flexible tube 140 is typically less than the hardness of the materials used for the self-retaining securement mechanism 120 and/or the connector conduit 130. The flexible tube 140 preferably includes a material that has a binding energy greater than about 400 kJ/mol.

The flexible tube 140 is defined by an outer diameter of between about 2 Fr. to about 6 Fr. and more preferably between about 3 Fr. to about 5 Fr. In one embodiment, the outer diameter of the flexible tube 140 is about 5 Fr. In a different embodiment, the outer diameter of the flexible tube 140 is about 4 Fr. In still a different embodiment, the outer diameter of the flexible tube 140 is about 3 Fr. Further, the flexible tube 140 includes an interior diameter of between about 0.01 Fr. to about 3 Fr. and more preferably between about 1 Fr. to about 2 Fr. In one embodiment, the interior diameter of the flexible tube 140 is about 1 Fr. In a different embodiment, the interior diameter of the flexible tube 140 is about 2 Fr. In still a different embodiment, the interior diameter of the flexible tube 140 is about 1.5 Fr.

Now turning to FIG. 7, the flexible tube 140 terminates at a tip 150 at the second end 116 of the stent 100. In one embodiment, the tip 150 includes the same material as the flexible tube 140. In a different embodiment, the tip 150 includes other materials discussed herein in connection with any portion of the stent 100. In still a different embodiment, the tip 150 may be made of a different material. The tip 150 is designed to be positioned adjacent the patient's bladder 112 and is shaped to facilitate removal therefrom. In contrast to many prior art stents, the tip 150 is designed to conform to the shape of the patient's passageway (e.g., ureter) and does not have a preformed coil, spiral, or loop shape.

In the embodiment depicted in FIG. 7, the tip 150 is provided in the form of a truncated triangle and includes two opposing sloped walls 152 that taper inwardly toward one another until terminating at a small opening 154. The tip 150 preferably has a smaller profile than the outer diameter of the flexible tube 140. Although depicted as a truncated triangle, the tip 150 may be other shapes and sizes as desired. Alternatively, the tip 150 may be omitted all together such that the flexible tube 140 is the end of the stent 100.

The use of one or more materials in the stent 100 having different hardness properties is important to realizing the advantages described herein. In one embodiment, the stent 100 is formed entirely of materials characterized by a hardness of less than about 40 Shore A. In a different embodiment, between about 75% to about 99% of the materials of the stent 100 are characterized by a hardness of less than about 40 Shore A. In another embodiment, between about 50% to about 75% of the stent 100 is characterized by a hardness of less than about 40 Shore A. In yet another embodiment, greater than about 70% of the stent 100 is characterized by a hardness of less than about 40 Shore A (all as determined using the ASTM D-2240 method).

In another embodiment, the stent 100 is formed entirely of materials characterized by a hardness of less than about 80 Shore A, or less than about 60 Shore A. In a different embodiment, between about 75% to about 99% of the stent 100 is characterized by a hardness of less than about 80 Shore A. In another embodiment, between about 50% to about 75% of the stent 100 is characterized by a hardness of less than about 80 Shore A. In yet another embodiment, greater than about 70% of the stent 100 is characterized by a hardness of less than about 80 Shore A (all as determined using the ASTM D-2240 method).

It should be recognized that the hardness of one or more portions of the stent 100 may be impacted by various factors. In one embodiment, the stent 100 includes a single material, whereby hardness of one portion of the stent 100 (e.g., the renal portion 104) is higher (i.e., more stiff) than that of one or more other portions of the stent 100 (e.g., the bladder portion 106). The perceived hardness may be caused by various factors including the specific material used, the diameter of the stent 100 over the length thereof, and/or the inclusion of wire or other reinforcement mechanisms within the stent 100. In one particular embodiment, the stent 100 includes a single material with a reinforcement mechanism (e.g., wire) disposed in a portion thereof to provide rigidity over a discrete length. Other portions of the stent 100 may not include the reinforcement mechanism, and thus, have a hardness parameter less than that of the portion having the reinforcement mechanism. In a different embodiment, the diameter of the stent 100 tapers from about 6 Fr. to about 4.5 Fr. The tapering of the stent 100 causes the portion having the larger diameter to be more stiff than the portion having the smaller diameter.

The hardness of the stent 100 may also be characterized in other ways. For example, in one embodiment, portions of the stent 100 include one or more materials defined by a hardness of less than about 100 Shore D. In another embodiment, one portion of the stent 100 is defined by a hardness of less than about 60 Shore A and a second portion of the stent 100 is defined by a hardness of less than about 75 Shore D. Although hardness parameters are discussed herein, the hardness or softness of portions of the stent 100 may include other parameters and characteristics, and the stent 100 herein is not limited thereby.

Figure 10:
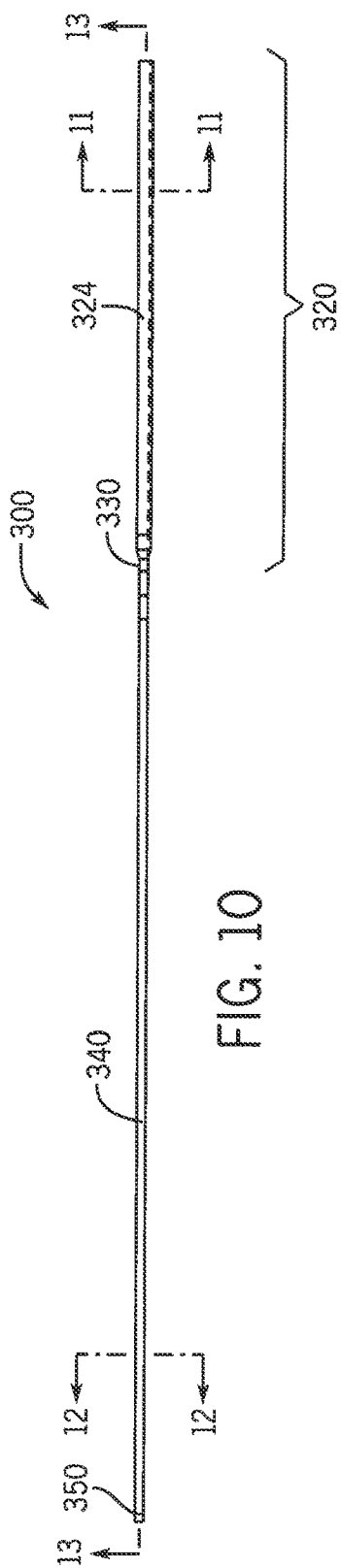
FIG. 10 is a top plan view of another embodiment of a stent.
Figure 12:
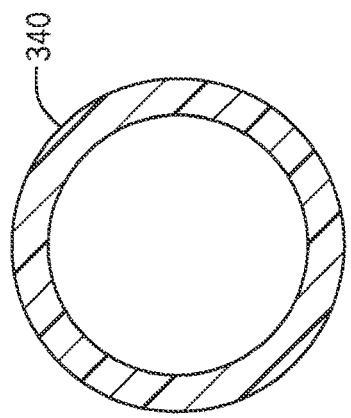
FIG. 12 is a cross-sectional view of an opposing end of the stent of FIG. 10 taken generally along the lines 12-12 of FIG. 10.
Figure 11:
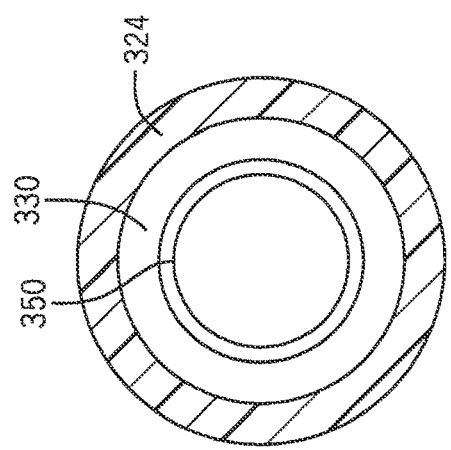
FIG. 11 is a cross-sectional view of an end of the stent of FIG. 10 taken generally along the lines 11-11 of FIG. 10.

As best seen in FIGS. 5 and 10, other embodiments of a stent are depicted. The stents 200, 300 are similar to the stent 100 described herein except for the below noted differences. In particular, the stents 200, 300 include a substantially straightened self-retaining securement mechanism 220, 320 disposed on a renal portion thereof. The self-retaining securement mechanisms 220, 320 each include a straightened portion 224, 324 as opposed to the J-shaped coil 122 of the stent 100. The self-retaining securement mechanisms 220, 320 are designed to be located adjacent the patient's kidney and to securely anchor the stent 200, 300 thereto.

Similar to the stent 100, the self-retaining securement mechanisms 220, 320 include a rigid material as compared to the other portions of the stents 200, 300. For example, suitable materials for use as the self-retaining securement mechanisms 220, 320 include any biocompatible materials having the hardness defined herein. Examples of suitable materials for the self-retaining securement mechanisms 220, 320 include polymers and copolymers such as polyurethane, polyamides, and various ethylene copolymers and block copolymers (e.g., ethyl vinyl acetate (EVA)). Other useful materials include biocompatible plastics, e.g., polyester, nylon based biocompatible polymers, polytetrafluoroethylene polymers, silicone polymers, polyurethane polymers, polyethylene polymers, and thermoplastic polymers.

The stents 200, 300 each include a tapered connector conduit 230, 330 that extends between the self-retaining securement mechanisms 220, 320 and tubular members 240, 340. Tips 250, 350 are optionally provided at ends of the stents 200, 300.

Figure 13:
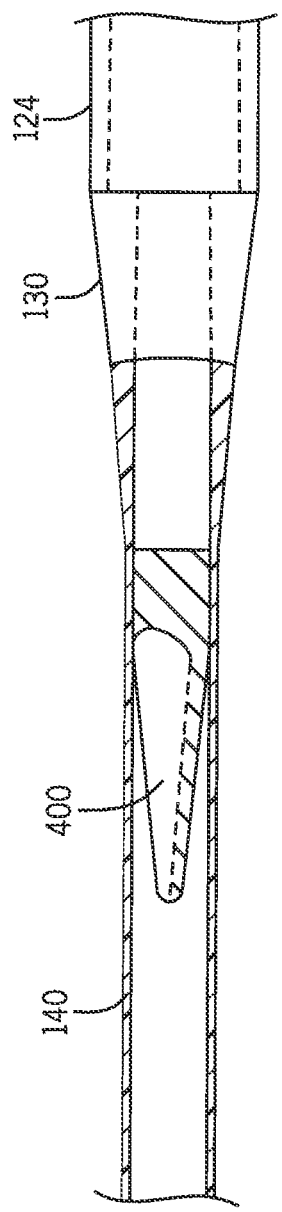
FIG. 13 is a cross-sectional side view of the stent of FIG. 10 having a valve therein taken generally along the lines 13-13 of FIG. 10.
Figure 14:
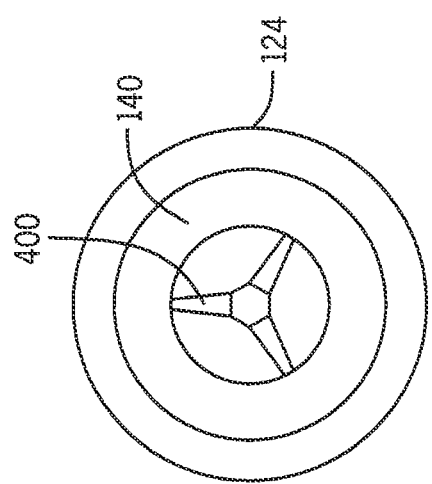
FIG. 14 is a front axial view of the stent of FIG. 10.

Now turning to FIG. 13, a valve 400 is disclosed for use with any of the stents 100, 200, 300 described herein. The valve 400 may be any number of valves including a one-way valve having a single leaflet, a single flap valve, or a ball valve. In a different embodiment, the valve 400 may include a bi-leaflet or tri-leaflet valve. In still a further embodiment, the valve 400 includes a valve with a spherical flap. In one embodiment, the valve 400 is preferably a one-way valve such that the valve 400 is designed to allow liquid to pass therethrough in a single direction (i.e., away from the patient's kidneys toward the patient's bladder). In a different embodiment, the valve 400 inhibits fluid flow in a direction longitudinally toward the renal portion 104 of the stent 100. In other embodiments, the valve 400 may be omitted all together. The valve 400 may be other types of valves that operate in the manner described herein.

The valve 400 may be positioned in the stent 100 in any suitable location. For example, in one embodiment, the valve 400 is positioned adjacent the connector conduit 130 (as shown in FIG. 13). In a further embodiment, the valve 400 is disposed adjacent the renal portion 104 (i.e., the rounded J-shaped coil 122 or straightened portion 124). In a further embodiment, the valve 400 is positioned adjacent the tip 150. It should be recognized that although the valve 400 is discussed in connection with the stent 100 of FIGS. 1-4, the valve 400 may be utilized with stents 200, 300 of the other embodiments.

One or more portions of the stent 100 may include a coating and/or may include a hydrophilic or hydrophobic material. In some embodiments, the stent is coated with a lubricious hydrophilic coating. Such a coating can be applied to any portion of the stent 100 to reduce irritation caused by contact with the surrounding tissue in the urinary tract and/or bladder. The coating is preferably compatible with the materials used. In one particular embodiment, the preferred coating is heparin, which is known to reduce infection, anti-calcification, and/or encrustation. In another embodiment, the stent 100 is coated with a coating intended to prevent calcification. In a different embodiment, the stent 100 is coated with a coating intended to prevent inflammation, and in a further embodiment, the stent 100 is coated with a coating intended to prevent infection.

One or more portions of the stent 100 may further include one or more radio opaque markers (not shown) to assist in inserting, positioning, and/or removing the stent 100. In one embodiment, one or more portions of the stent 100 are made of a radio opaque material. In a different embodiment, one or more radio opaque markers may be added to portions of the stent 100. For example, a radio opaque marker may be disposed adjacent the self-retaining securement mechanism 120 disposed on the renal portion 104 of the stent 100. The marker may be visible to a physician under X-ray, flouroscopy, or other visual aids. The stent 100 may include one or more radio opaque markers on other portions thereof, including on the connector conduit 130, flexible conduit 140, and/or the tip 150. In use, the physician may use the mark(s) to facilitate placement of the stent 100 in the patient and more particularly, to assist in guiding the self retaining securement mechanism 120 into the patient's kidney 110.

One or more portions of the stent 100 may include a catch (not shown) or other mechanism to facilitate insertion of the stent 100 into the patient. The catch is designed to interact with a deployment mechanism such as a guidewire (not shown) to assist in positioning the stent 100. In one embodiment, the self-retaining securement mechanism 120 of the stent 100 is inserted into a patient by using a guidewire that extends from the bladder 112, through the ureter 108, and into the kidney 110. The guidewire may extend substantially along the length of the self-retaining securement mechanism 120, which causes the J-shaped coil 122 to temporarily deform into a substantially linear shape. A pusher or other similar tool may be placed over the guidewire adjacent to a portion of the stent 100. In one embodiment, the pusher exerts a force on a portion of the coil 122 (e.g., the end 114) to appropriately locate the stent 100 proximate to the kidney. It is contemplated that the pusher may be substantially longer than a standard pusher. Typical pushers push end-to-end whereas the pusher may be designed to fit over the distal portion of the stent and go into the ureter. In a different embodiment, the pusher is positioned adjacent the valve 400 to assist in the positioning thereof. In a further embodiment, the pusher may contact or otherwise move other portions of the stent 100 to assist in the positioning thereof. After the stent 100 is positioned, the guidewire and pusher are removed, which causes the J-shaped coil 122 to bend into a shape similar to the shape depicted in FIG. 3 or any other shape designed to self retain and secure the placement of the stent 100 in the kidney.

The stent 100 may be positioned in the patient using a variety of other methods, techniques, and/or tools. For example, the stent 100 may be utilized in conjunction with the guidewire described in U.S. patent application Ser. No. 12/660,891, filed on Mar. 5, 2010, and incorporated by reference in its entirety. That is, the stent can be placed through a sheath, even without a guidewire.

The present invention has been described in terms of one or more preferred embodiments, and it should be appreciated that many equivalents, alternatives, variations, and modifications, aside From those expressly stated, are possible and within the scope of the invention. Any of the embodiments described herein may be modified to include any of the structures or methodologies disclosed in connection with different embodiments.

We claim:

1. A stent, comprising:
a renal portion sized to be disposed proximate a patient's kidney and having a hardness that is at least 20 Shore A and no greater than 90 Shore A, the renal portion comprising a self-retaining securement mechanism;
a bladder portion sized to be disposed proximate a patient's bladder and characterized by a hardness less than that of the renal portion, the hardness of the bladder portion being at least 5 Shore A, and less than 20 Shore A, wherein the bladder portion terminates at a tip within the patient's bladder, and the tip lacks a self-retaining securement mechanism; a tapered connector conduit disposed between the renal portion and the bladder portion, wherein the tapered connector has an outer diameter that tapers from an outer diameter of the renal portion at a connection with the renal portion down to an outer diameter of the bladder portion at a connection with the bladder portion; and
a one-way valve disposed within the stent to guide liquid from the renal portion toward the bladder portion of the stent and inhibit flow from the bladder portion toward the renal portion, wherein the valve is disposed between the renal portion and the bladder portion.

2. The stent of claim 1, wherein the self-retaining securement mechanism has a substantially smooth exterior and is configured to maintain a substantially straight shape.

3. The stent of claim 1, wherein the tapered connector conduit is characterized by a hardness that lessens moving from the renal portion toward the bladder portion.

4. The stent of claim 1, wherein the renal portion comprises a first material and the bladder portion comprises a second material different from the first material.

5. The stent of claim 4, wherein the first material is polyurethane.

6. The stent of claim 5, wherein the second material is silicone.

7. The stent of claim 5, wherein the tip includes sloped walls and an opening therein, and the diameter of the opening is smaller than an interior diameter of the bladder portion.

8. A stent, comprising:
a renal portion sized to be disposed proximate a patient's kidney, wherein the renal portion of the stent has a first outer diameter that is substantially constant along the length of the renal portion, and the renal portion comprises a self-retaining securement mechanism;
a bladder portion sized to be disposed proximate a patient's bladder, wherein the bladder portion is characterized by a hardness less than that of the renal portion, the hardness of the bladder portion being at least 5 Shore A, and less than 30 Shore A, wherein the bladder portion of the stent has a second outer diameter that is substantially constant along the length of the bladder portion;

a tapered connector conduit disposed between the renal portion and the bladder portion, wherein the tapered connector has an outer diameter that tapers from the first outer diameter at a connection with the renal portion down to the second outer diameter at a connection with the bladder portion; and a one-way valve disposed adjacent the tapered connector conduit, wherein between about 75% to about 99% of the stent is characterized by a hardness that is at least 30 Shore A, and is less than about 80 Shore A, and wherein the valve facilitates fluid flow only in one direction through the conduit.

9. The stent of claim 8, wherein the connector conduit comprises a plurality of materials.

10. The stent of claim 8, wherein the connector conduit is formed of a material along a length thereof, and the bladder portion is formed of the material along a length thereof.

11. The stent of claim 8, further comprising a wire disposed within the renal portion forming a reinforcement mechanism to secure the stent in a fixed position relative to the patient.

12. A stent, comprising:
a renal portion comprising a self-retaining securement mechanism having a first hardness value that is characterized by a hardness that is at least 30 Shore A and no greater than 90 Shore A, wherein the renal portion of the stent has a first outer diameter that is substantially constant along the length of the renal portion;
a flexible tube defining a bladder portion having a second hardness value that is less than that of the first hardness value and is characterized by a hardness that is at least 5 Shore A and less than 30 Shore A, wherein the bladder portion is configured to terminate within the patient's bladder, the bladder portion terminates at a tip that lacks a self-retaining securement mechanism, and the bladder portion of the stent has a second outer diameter that is substantially constant along the length of the bladder portion;
a tapered connector conduit disposed between the renal portion and the bladder portion, wherein the tapered connector has an outer diameter that tapers from the first outer diameter at a connection with the renal portion down to the second outer diameter at a connection with the bladder portion; and
a one-way valve disposed in the stent that inhibits fluid flow from the bladder portion into the self-retaining securement mechanism.

13. The stent of claim 12, wherein the valve is disposed adjacent the self-retaining securement mechanism.

14. The stent of claim 12, wherein the valve is disposed within the tapered connector conduit.

15. The stent of claim 14, wherein the valve is selected from the group consisting of a single leaflet, a bi-leaflet, or a tri-leaflet.

16. The stent of claim 12, wherein the stent includes a coating on a portion thereof.

17. The stent of claim 12, wherein the stent includes at least one radio opaque marker.

* * * * *